US008344334B2

(12) United States Patent
Coker et al.

(10) Patent No.: US 8,344,334 B2
(45) Date of Patent: Jan. 1, 2013

(54) APPARATUS AND METHOD FOR DETECTION AND MEASUREMENT OF TARGET COMPOUNDS SUCH AS A FOOD TOXIN

(75) Inventors: Raymond Douglas Coker, Bromley (GB); John Tetteh, Rochester (GB); Michael Paul Andreou, Horsham (GB)

(73) Assignee: Toximet Limited, Kent (GB)

( * ) Notice: Subject to any disclaimer, the term of this patent is extended or adjusted under 35 U.S.C. 154(b) by 94 days.

(21) Appl. No.: 12/681,863

(22) PCT Filed: Sep. 22, 2008

(86) PCT No.: PCT/GB2008/050850
§ 371 (c)(1),
(2), (4) Date: Jun. 14, 2010

(87) PCT Pub. No.: WO2009/047549
PCT Pub. Date: Apr. 16, 2009

(65) Prior Publication Data
US 2010/0264332 A1 Oct. 21, 2010

(30) Foreign Application Priority Data
Oct. 8, 2007 (GB) .................. 0719602.5

(51) Int. Cl.
*G01N 21/64* (2006.01)
(52) U.S. Cl. .................................................. 250/459.1
(58) Field of Classification Search ............ 250/458.1, 250/459.1
See application file for complete search history.

(56) References Cited

U.S. PATENT DOCUMENTS

| 5,178,832 | A | 1/1993 | Phillips et al. |
| 5,866,430 | A * | 2/1999 | Grow ............................ 506/6 |
| 5,989,835 | A | 11/1999 | Dunlay et al. |
| 6,485,413 | B1 * | 11/2002 | Boppart et al. ............... 600/160 |
| 6,637,438 | B1 | 10/2003 | Lane |
| 7,242,468 | B1 * | 7/2007 | Zhang ............................ 356/301 |
| 7,515,269 | B1 * | 4/2009 | Alexander et al. ............. 356/445 |
| 2001/0046712 | A1 | 11/2001 | Hang et al. |
| 2003/0127609 | A1 | 7/2003 | El-Hage et al. |
| 2004/0029210 | A1 | 2/2004 | Robillot et al. |
| 2006/0029941 | A1 | 2/2006 | Koo et al. |
| 2006/0046313 | A1 | 3/2006 | Roth et al. |
| 2006/0146317 | A1 | 7/2006 | Aklian |
| 2009/0011403 | A1 * | 1/2009 | Smith et al. ....................... 435/5 |

FOREIGN PATENT DOCUMENTS

EP 1533607 6/2005
(Continued)

OTHER PUBLICATIONS

Golden et. al., "A portable array biosensor for food safety," 2004, SPIE Proceedings, vol. 5587, pp. 241-244.*

(Continued)

*Primary Examiner* — Kiho Kim
(74) *Attorney, Agent, or Firm* — Occhiuti Rohlicek & Tsao LLP

(57) ABSTRACT

A method for the detection or determination of a target comprising a plurality of target compounds, or derivatised target compounds, said method comprising: immobilizing said target on a carrier, directing radiation at said target, said radiation being selected to cause said target to emit a relevant radiation, detecting said relevant radiation emitted by said target, and analyzing said detected radiation to identify and/or quantify the plurality of target compounds in said target.

37 Claims, 5 Drawing Sheets

FOREIGN PATENT DOCUMENTS

| | | |
|---|---|---|
| EP | 0956497 | 8/2005 |
| EP | 1592812 | 4/2009 |
| WO | WO89/03037 | 4/1989 |
| WO | WO01/28367 | 4/2001 |
| WO | WO02/23196 | 3/2002 |
| WO | WO02/065115 | 8/2002 |
| WO | WO2004/090505 | 10/2004 |
| WO | WO2006/123189 | 11/2006 |
| WO | WO2007/078635 | 7/2007 |

OTHER PUBLICATIONS

Thompson et al., "Measurement of fumonsins in corn with a fiber-optic fluoroimmunosensor," 1997, SPIE Proceedings, vol. 1997, pp. 532-538.*

Courcoux et al., "Simultaneous decomposition of multivariate images using three-way data analysis Application to the comparision of cereal grains by confocal laser scanning microscopy," 2002, Chemometrics and Intelligent Laboratory Systems, vol. 62, pp. 103-113.*

Rodriguez-Cuesta et al., "Determination of carbendazim, fuberidazole and thiabendazole by three-dimentionsal excitation-emission matrix fluorescence and parallel factor analysis," 2003, Analytica Chimica Acta, vol. 491, pp. 47-56.*

Ngundi et al., "Array Biosensor for detection of ochratoxin A in Cereals and Beverages," 2005, Analytical Chemistry vol. 77, No. 1, pp. 148-154.*

* cited by examiner

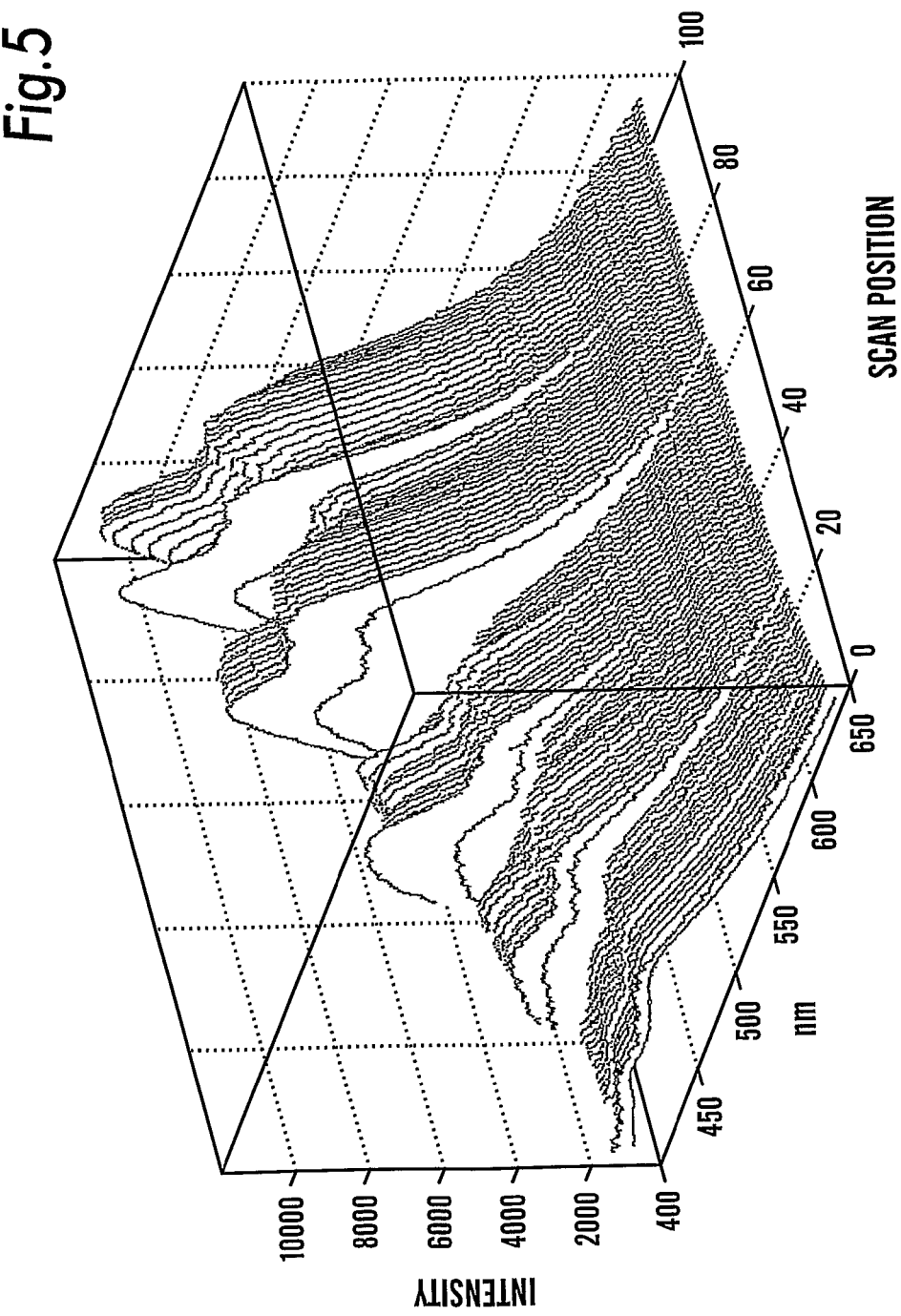

APPARATUS AND METHOD FOR DETECTION AND MEASUREMENT OF TARGET COMPOUNDS SUCH AS A FOOD TOXIN

CROSS-REFERENCE TO RELATED APPLICATIONS

This application is the National Stage of International Application No. PCT/GB2008/050850, filed on Sep. 22, 2008, which claims the priority of United Kingdom Application No. 0719602.5, filed on Oct. 8, 2007. The contents of both applications are hereby incorporated by reference in their entirety.

FIELD OF THE INVENTION

The present invention relates to apparatus and method for the detection, and quantification of target compounds such as food toxins such as mycotoxins, such as aflatoxins. The apparatus may also be used for detection of other toxins and non-toxic compounds of interest.

BACKGROUND OF THE INVENTION

Mycotoxins are toxic metabolic by-products of fungi which can dangerously contaminate a wide variety of human foods and animal feeds, including edible nuts, oilseeds, cereal grains, and forages and products derived from them. Among the most significant are aflatoxins, a group of closely-related mycotoxins produced by the fungi *Aspergillus flavus* and *A. parasiticus*. Not all isolates of the fungus produce aflatoxins; thus, the mere presence of *A. flavus* or *A. parasiticus* does not mean that aflatoxins will be present in the substrate. Accordingly direct determination of mycotoxin level is an important aspect of quality control in foods and feeds.

Such measurements have conventionally been carried out by the use of high performance liquid chromatography (HPLC). However in those cases where HPLC equipment is not available or appropriate, determination by thin layer chromatography (TLC) is also possible. Commercial scanners are available for mycotoxin determination after TLC separation, using mercury lamps with an emission wavelength of 366 nm as a light source to stimulate fluorescence, which is detected and quantified by photo-multipliers.

For quantitative testing there are also radioimmunoassay techniques and immunochemically-based techniques such as enzyme-linked immunosorbent assay (ELISA) methods.

Qualitative detection of mycotoxins can be carried out using small chromatographic columns (traditionally called 'minicolumns'). Various minicolumn methods have been adopted as official tests of the AOAC International (Association of Official Analytical Communities). The major uses of minicolumn tests for aflatoxin are as "go" or "no go" field tests to accept or reject for example a truckload of peanuts or corn, and as central laboratory screening tests to avoid the need to quantitatively test samples that do not contain a detectable amount of aflatoxin.

In our copending patent application PCT/GB2006/050115 we describe apparatus for the detection or determination of a target comprising a target compound, a derivatised target compound or target compound-stimulated moiety, said apparatus comprising: means for mounting a sample cartridge, which sample cartridge comprises a packing or coating capable of immobilising or isolating the target in a layer or band, an excitation unit for emitting radiation that excites fluorescent radiation, a detection unit that is sensitive to said fluorescent radiation, and means for relatively moving the mounting means and the detection unit whereby the fluorescent radiation from the target may be sensed.

Whilst the apparatus described in patent application PCT/GB2006/050115 is extremely useful, it only detects a single target compound or target compound-stimulated moiety at a time. Whist one tries to have only a single target compound, in practice there are often more than one target compounds present and it would be useful to be able to identify and quantify the plurality of target compounds.

It would be even more useful to be able to be able to detect one or more than one target compound or derivatised target compound at a time and one or more than one target compound at a time which does not produce fluorescent radiation.

Not all target compounds of interest fluoresce and it would be useful to identify such target compounds.

SUMMARY OF THE INVENTION

According to a first aspect, the present invention provides a method for the detection or determination of a target comprising a plurality of target compounds, or derivatised target compounds, said method comprising:
immobilising said target on a carrier,
directing radiation at said target, said radiation being selected to cause said target to emit a relevant radiation,
detecting said relevant radiation emitted by said target, and
analysing said detected radiation to identify and/or quantify the plurality of target compounds in said target.

Preferably said detected radiation comprises a spectrum, or mixture of spectra, and the spectral data is stored as a matrix of data with rows of wavelength and columns of spectral acquisition positions across the target.

Preferably said spectral data is analysed using multivariate data decomposition such as Principal Component Analysis to decompose the data.

Preferably the matrix of decomposed data is compared with reference spectra of known compounds to provide matching spectra. The matching reference spectra in the data matrix may be used to identify the target compounds. The matching reference spectra in the data matrix may be used to deduce the relative concentration of target compounds.

Preferably a least squares method is used to estimate the absolute concentrations from the relative concentration using the reference spectrum of a known concentration of a known reference target compound.

Preferably the degree of correlation between the reference and predicted spectrum within a spectral range provide qualitative information about the target.

According to a second aspect, the present invention provides apparatus for the detection or determination of a target comprising a plurality of target compounds, or derivatised target compounds, said apparatus comprising:
means for mounting a carrier, the target being immobilised on said carrier,
an excitation unit for emitting radiation and directing said radiation at said target, said radiation being selected to cause said target to emit a relevant radiation,
a detection unit that is sensitive to said relevant radiation emitted by said target, and means to analyse said detected radiation to identify and/or quantify the plurality of target compounds in said target.

Preferably said detection unit includes a spectrometer for producing a spectrum of said detected radiation.

Said detection unit may include an optical fibre for passing the radiation to the spectrometer.

The apparatus may include data storage means adapted to store said spectrum of the detected radiation as a matrix of data with rows of wavelength and columns of spectral acquisition positions across the target.

Preferably said means to analyse said detected radiation is adapted to analyse said spectral data using multivariate data decomposition.

Preferably said means to analyse said detected radiation is adapted to analyse said spectral data using Principal Component Analysis to decompose the data.

In one arrangement said excitation unit for emitting radiation and directing said radiation at said target comprises means for emitting radiation such as to cause fluorescence in said target.

In another arrangement said excitation unit for emitting radiation and directing said radiation at said target comprises means for emitting radiation such as to cause Raman scattering in said target.

Means may be provided for relatively moving the mounting means and the detection unit whereby the relevant radiation from different points of the target may be sensed.

According to a third aspect, the present invention provides apparatus for the detection or determination of a target comprising a target compound or a derivatised target compound said apparatus comprising:

means for mounting a carrier, the target being immobilised on said carrier, an excitation unit for emitting radiation and directing said radiation at said target, said radiation being selected to cause Raman scattering in said target whereby to emit a relevant radiation, a detection unit that is sensitive to said relevant radiation emitted by said target, and means to analyse said detected radiation to identify and/or quantify the target compound.

Preferably said detection unit comprises a spectrometer to provide a spectrum of the radiation received.

Said detection unit may include an optical fibre for passing the radiation to the spectrometer.

Preferably said excitation unit comprises a laser to provide a laser beam of suitable wavelength to promote Raman excitation in the target.

Means for relatively moving the mounting means and the detection unit may be provided whereby the relevant radiation from different points of the target may be sensed.

Preferably said means for mounting said target comprises means for immobilising or isolating said target in a packing or coating or on a surface, or a rod coated with the adsorbent for the target, or a tube or cuvette coated internally with the adsorbent for the target, or a cartridge packed with a mineral or polymer adsorbent for the target.

The means for mounting the target may comprise a slide of glass, metal or plastic.

Preferably the means for relatively moving the mounting means and the detection unit comprises means for relatively moving them in such a manner as to scan the detection unit past all of the target.

Preferably the means for relatively moving the mounting means and the detection unit comprises means for relatively moving them in a linear direction and means for relatively rotating them.

The apparatus may further comprise a processing unit that converts the output of the detector unit into a readable value related to the amount of target compound immobilised in the packing or coating or on a surface.

The carrier may comprise for example a cartridge. The term "carrier" may, however include any removable unit capable of supporting a packing or coating of adsorbent on which a layer of toxin can be immobilised. Suitable 'carriers' include small glass mini-columns or plastics tubes containing suitable mineral or polymer adsorbent packings, and cuvettes or rods or slides with internal or external coatings of adsorbent.

BRIEF DESCRIPTION OF THE DRAWINGS

Preferred embodiments of the invention will now be described with reference to the accompanying drawings in which:

FIG. 5 is a spectral profile of raw fluorescent spectral data in respect of a target comprising a plurality of target compounds

DETAILED DESCRIPTION OF THE PREFERRED EMBODIMENTS OF THE INVENTION

Figure 1:
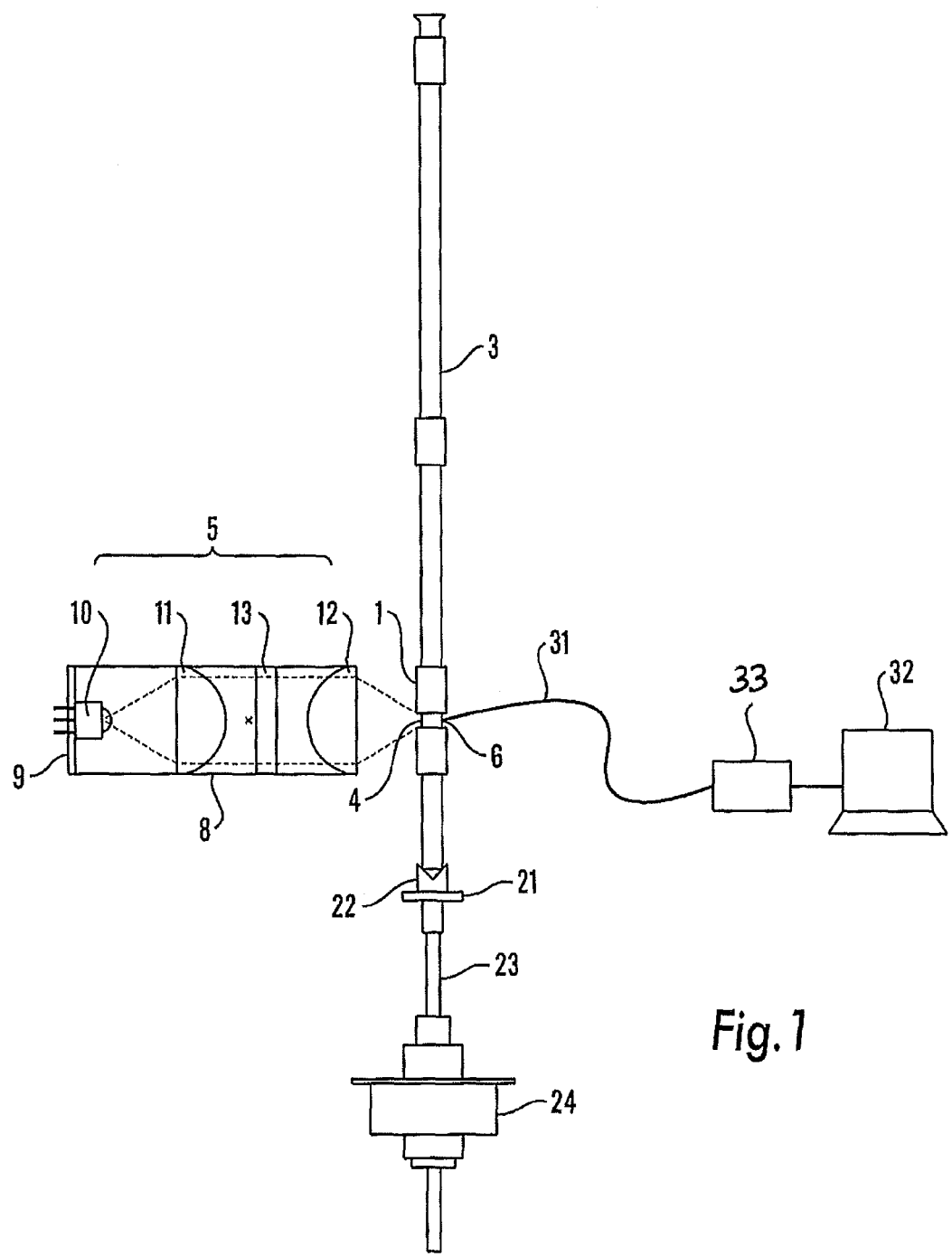
FIG. 1 is a schematic side view of the principal components of a preferred embodiment of apparatus according to the invention

One embodiment of the invention is based on the knowledge that radiation of certain wavelengths excites target compounds such as food components or contaminants such as mycotoxins to fluoresce, and that the wavelength of the emitted fluorescent light is significantly different (usually longer) than the excitation wavelength. The amount of light emitted is proportional to the amount of the substance, a measurement of the amount of light emitted can be used to quantify the amount of target compounds, such as mycotoxins, immobilised in a sample cartridge and we use an analysis of the spectrum to provide information about the identity of the plurality of toxins present.

We have now discovered that we can use Raman spectroscopy for similar analysis in respect of target compounds which do not fluoresce. Raman spectroscopy is a spectroscopic technique which relies on inelastic scattering, (Raman scattering) of monochromatic light, usually from a laser in the visible, near infrared, or near ultraviolet range. For example, the laser may be a HeNe source with a wavelength of 633 nm (visible red) or a NIR diode with a wavelength of 785 nm. The laser light interacts with phonons or other excitations in the system, resulting in the energy of the laser photons being shifted up or down. The shift in energy gives information about the phonon modes in the system.

A preferred embodiment of the invention involves the extraction of a target such as a plurality of chemical toxins from food, the immobilisation of the toxins as a layer or band in a columnar packing or coating or as a layer on the surface of a slide or other surface.

In using a fluorescence method, the method involves the illumination of the band, typically with UV radiation, at an appropriate wavelength to excite the emission of fluorescent light by the band, the detection of the fluorescence and analysis of the fluorescent spectra and the analysis of the detected signal to provide the identity and measurement of the concentration of the plurality of toxins (typically in parts per billion).).

In using Raman spectroscopy, the method involves passing suitable laser radiation to the layer, the detection of the Raman effect produced, analysis of the spectra to provide the identity and measurement of the concentration of the plurality of toxins (typically in parts per billion).

Accordingly apparatus for use in a fluorescence typically comprises a holder for a sample cartridge (e.g. mini-column, plastic, glass or metal tube, cuvette or rod) which comprises a packing or coating capable of immobilising or isolating one or more target compounds in a layer or band, an excitation unit that emits radiation that excites fluorescence in a target compound or derivatised target compound immobilised or isolated in the packing or coating, a detection unit that is sensitive to radiation emitted by each fluorescing target compound, means for relatively moving the sample cartridge and the detection unit whereby the radiation may be sensed, and a processing unit that converts the output of the detector unit into a readable value related to the amount of target compound immobilised in the layer or band. The output may be fed to a computer for analysis or to an associated display screen. The relative movement of the sample cartridge and the detection unit doesn't just allow the radiation to be sensed by relatively aligning them but allows the fluorescing target compound to be scanned thereby ensuring that the extent of the fluorescing target compound is detected to give a quantitative measure of the amount of fluorescing target compound or compounds present.

Typically the housing also contains a power source, or means for connecting to a power source, to power the excitation unit, the detection unit and the processing unit.

Typical 'cartridges' for use in the apparatus comprise transparent tubes packed with one or more layers of adsorbent(s), the adsorbents being polymers tailored to isolate and immobilise the target compounds which are to be detected. In use, a solution extracted from a sample potentially contaminated with mycotoxins, or other target, is passed through the detector tube or is transported through the tube by a suitable solvent or solvent mixture. The essence of the cartridge system is that mycotoxins of interest are immobilised by a specific adsorbent so that the mycotoxin is present in the cartridge as a layer or band which can be detected by fluorescence. Some mycotoxins are naturally fluorescent, whereas others require the addition of a derivatising agent to the solution or to the column in order to produce a fluorescent derivative.

As the mycotoxin mixture passes through the apparatus and is contacted by the various adsorbents, selected mycotoxins are immobilized.

Cartridges commercially available for the detection of aflatoxins typically are packed with layers of calcium sulphate, silica gel, alumina, Florisil™ and calcium sulphate, with a suitable plug at each end to hold the layers in the column. For example FIG. 1 of the our Patent application PCT/GB2006/050115 shows a minicolumn of borosilicate glass selected for minimal blue fluorescence under UV black light (365 nm), which is 5 mm outer diameter, 3.4 mm inner diameter and 12 cm long, fused to a 3 cm length of 14 mm outer diameter borosilicate glass to act as a reservoir.

This immobilization phenomenon also enables separation of mycotoxin(s) of interest from interfering compounds. Interfering compounds are most commonly other fluorescent species. However substances which quench the fluorescence of the analyte and/or interfere with the excitation of the analyte are also considered interfering compounds for the purposes of this disclosure.

A variety of mycotoxins can be immobilised by selecting appropriate minerals including bayerite, pseudoboehmite, gibbsite, boehmite, bauxite, and acidic, basic or neutral alumina A cartridge for ochratoxin A, for example, may comprise (beginning at the bottom of the column): Blue Tac plug (0.3 cm); dry sodium sulphate (1 cm); acid washed sand (0.5 cm); pseudoboehmite (0.5 cm); dry sodium sulphate (2.0 cm).

Cartridges for the immobilisation of mycotoxins, and other targets, may comprise tailored polymers. A cartridge for the aflatoxins, for example, may comprise a polymer derived from the functional monomer methylene bisacrylamide. Similarly, a cartridge for ochratoxin A may comprise a polymer derived from the functional monomers itaconic acid and diethyl aminoethyl methacrylate.

The same or similar arrangement of cartridges and adsorbents may be used for analysis using Raman spectroscopy, but in an alternative arrangement the cartridges are replaced by a carrier comprising a surface, for example a glass or plastic or metal slide or rod on which the target compound or target compounds are deposited. Thus, in the apparatus for detecting Raman spectra, we prefer to analyse target compounds which are immobilised by being deposited onto a surface such as a glass or plastic or metal slide or rod. The surface is preferably coated with an appropriate adsorbent and/or surface enhancing agent such as colloidal gold, to enhance the intensity of the Raman spectra.

We will describe FIGS. 1 and 2 which show the general form of the apparatus. In a preferred embodiment of the apparatus, shown in FIGS. 1 to 3. The apparatus is adapted to allow a sample-containing carrier to be relatively movable with respect to the remainder of the apparatus to allow a 360° assessment of the sample.

As shown in FIG. 1, a tubular holder 1 is mounted on a support platform to receive a cartridge 3. The cartridge 3 contains toxins as described earlier.

There is provided an excitation unit 5.

If the apparatus is using fluorescence to analyse the toxins, the excitation unit 5 is an excitation unit of the type shown in FIGS. 1 and 2 which provides radiation of a wavelength (e.g. visible light or ultra violet light, Xenon lamps or light emitting diodes with a substantial UV content or UV-emitting diodes are suitable sources) to stimulate fluorescence in the target toxins.

If the apparatus is using a Raman method to analyse the toxins, in place of the excitation unit shown in FIGS. 1 and 2, there is a Raman excitation unit which provides radiation of a wavelength to stimulate the Raman effect and provide Raman scattering by excited phonons in the toxins. The Raman excitation unit is preferably a laser which provides a laser beam of suitable wavelength in the visible, near infrared (NIR), or near ultraviolet range. For example, the laser may be a HeNe source with a wavelength of 633 nm (visible red) or a NIR diode with a wavelength of 785 nm The holder 1 has a first side aperture 4 to allow excitation energy from the excitation unit 5 to impinge on the layer of toxins through the wall of the cartridge 3.

A second side aperture 6, at e.g. 90° to but in the same horizontal plane as aperture 4, allows fluorescent radiation or Raman radiation as appropriate to be emitted from the toxin layer to be captured by a an optical fibre 31 aligned with the aperture 6. The optical fibre 31 passes the detected radiation to a suitable spectrometer 33. The spectrometer 33 provides a spectrum of the detected radiation (an appropriate spectrometer is used for detecting the fluorescent or Raman signal.

The signal from the spectrometer 33 is passed to a separate computer 32 or, alternatively, to software embedded within the instrument, for analysis.

The cartridge 3 is positioned within the holder 1 so that the immobilised layer of toxin is in, or overlaps, the same plane as the apertures 4 and 6.

The excitation unit 5 used to provide fluorescence (illustrated in FIGS. 1 and 2) comprises an optical tube 8, with light-absorbing interior surfaces, aligned with the aperture 4. The end of the optical mount 8 remote from the holder 1 is closed by a circuit board 9 with electrical connections for a light (preferably UV) emitting diode mounted on the board 9 within the tube 8. Within the tube 8 a collimating lens 11 collimates the radiation emitted by the diode 10, and the collimated radiation is brought to a focus within the holder 1 via the aperture 4 by a lens 12 at the other end of the tube 8. Interposed between the lenses 11 and 12 is an interference filter 13 which passes radiation with a band of energy suitable to excite fluorescence in the intended target. Suitably the filter 13 is slidable within slots in the tube 8 so that it can be replaced easily or changed to provide a different characteristic wavelength band for excitation.

Although we have illustrated the apparatus with a cartridge 3 comprising a glass mini column, where the apparatus is for use with Raman spectroscopy, the toxins will more usually be deposited on a carrier comprising a surface such as a slide or rod made of glass or plastic or metal. In the case of a slide or rod, the toxins are immobilised on the surface of the slide or rod or more usually on a coating thereon.

Figure 2:
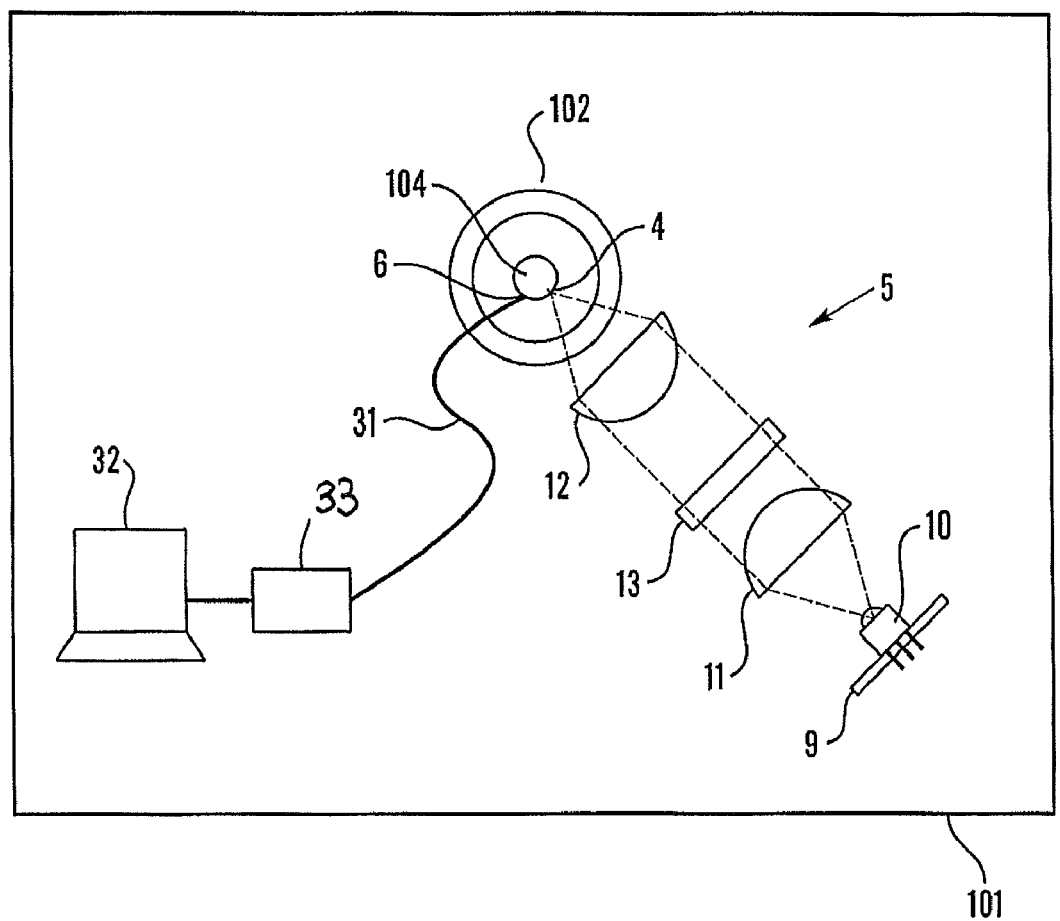
FIG. 2 is a schematic plan view of the arrangement of FIG. 1.

In use of the apparatus of FIGS. 1 and 2, when the cartridge, rod or slide 3 is placed into the holder 1, its lower end locates against a support plate 21. Because the position of the immobilised toxin layer in the cartridge or slide may vary in successive analyses, the plate 21 is preferably adjustable vertically up and down so that the toxin layer can be brought into the plane of the apertures 4 and, 6. Additionally, vertical movement allows the system to be used to investigate multiple bands in which different toxins are immobilised on stacked layers of adsorbents.

The fluorescence or Raman radiation emanating from the emission aperture 6 arises from the small part of the toxin layer that is exposed to the radiation at the excitation aperture 4. The radiation produced by fluorescence or Raman scattering as appropriate is then transmitted through along the optical fibre 31 to the spectrometer 33. By arranging for the cartridge, slide or rod to be rotatable and moveable vertically relative to the excitation and emission apertures means that the small part of the toxin that receives the excitation radiation and is viewed changes during rotation and vertical movement (i.e. the small part of the toxin viewed is scanned across the surface of the toxin) so that readings can be taken from the whole of the toxin layer as it is exposed in the excitation aperture 4. Suitably the end of the cartridge/slide/rod is firmly located in a gripping socket 22 mounted on the support plate 21, so that rotation of the support plate 21 also rotates the cartridge/slide/rod 3.

The rotational and vertical motions are conveniently combined as the support plate 21 is mounted on a screw-threaded rod 23 which is driven by an actuator motor 24 in the form of a digital linear actuator. Accordingly, rotation of the rod 23 both rotates the support plate 21 and moves it vertically. It is important that the pitch of the thread of the rod 23 is restricted to a value at which rotation of the cartridge, slide or rod through 360° does not move the toxin layer beyond the window of the apertures 4, 6.

In practice, because of the variable position of the immobilised band of toxin in the cartridge, slide or rod, the support plate 21 is typically set at it lowest position when a cartridge, slide or rod is placed into the holder 1 and engaged with the gripper 22. The motor 24 is then actuated to move the cartridge or slide upwardly while the detection unit observes the fluorescence/Raman radiation emanating from the aperture 6.

The systems then 'hunts' for the location of the region or regions of higher intensity, which will reveal the presence of the toxins. In the region of higher intensity, the spectrometer produces many spectra during the vertical movement and rotation of the cartridge, slide or rod.

FIG. 5 shows an example of fluorescent spectra for a target compound found in the form of a number of aflatoxins in a column (although similar considerations apply if the spectra are Raman spectra). In this case the graph is a three dimensional graph showing the intensity and wavelength of the spectra in two dimensions, the third dimension showing the detected spectra for different scanning positions on the column.

Figure 3:
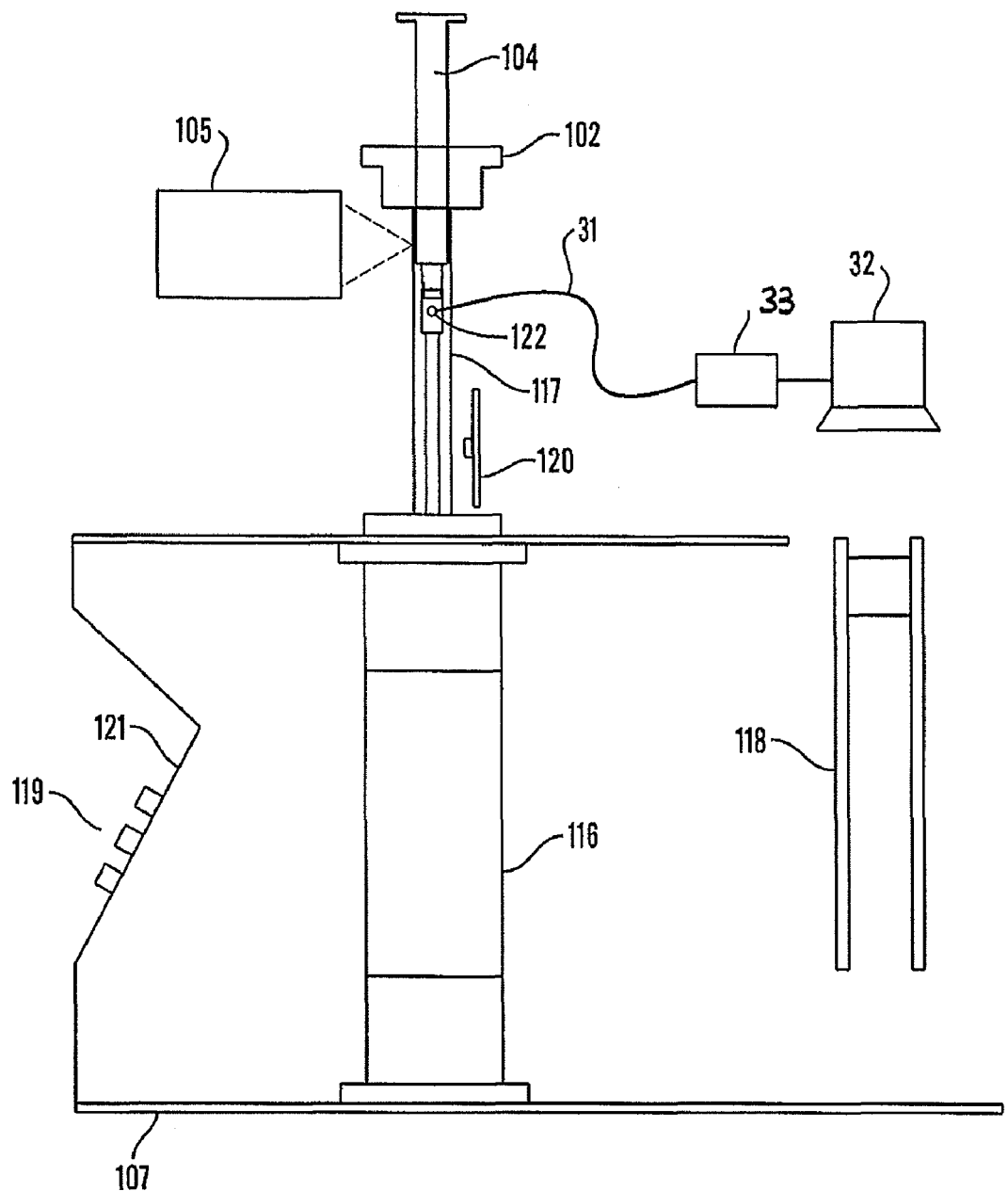
FIG. 3 is a side view of a further preferred embodiment, of apparatus according to the invention.

In an alternative physical arrangement shown in FIG. 3, the apparatus of the invention is contained within a generally rectangular housing 107. Within the housing is mounted a chassis. The top of the chassis mounts a mounting means 102 for mounting a sample cartridge in the form of a cartridge, rod or slide 104. The mount 102 may be adapted so as to mount other types of sample holding cartridges or containers.

The rectangular housing 107 extends (not shown) over the top of the mount 102 and excitation unit 106 and has a suitable aperture on the top surface thereof through which the cartridge, rod or slide 104 may be inserted into the mounting means 102.

Stepper motors 116 are arranged so as to rotate or axially move the cartridge support tube 117 in steps (which may be merged so as to rotate or move the mounting means 102 smoothly).

The stepper motors 116 are controlled by electronic components mounted on one or more printed circuit board 118. The manual input is provided by buttons or switches 119 mounted on the front face of the rectangular housing 107, and the information output may be via a suitable electronic coupling. A display 121 is also mounted on the front face of the rectangular housing 107

Figure 4:
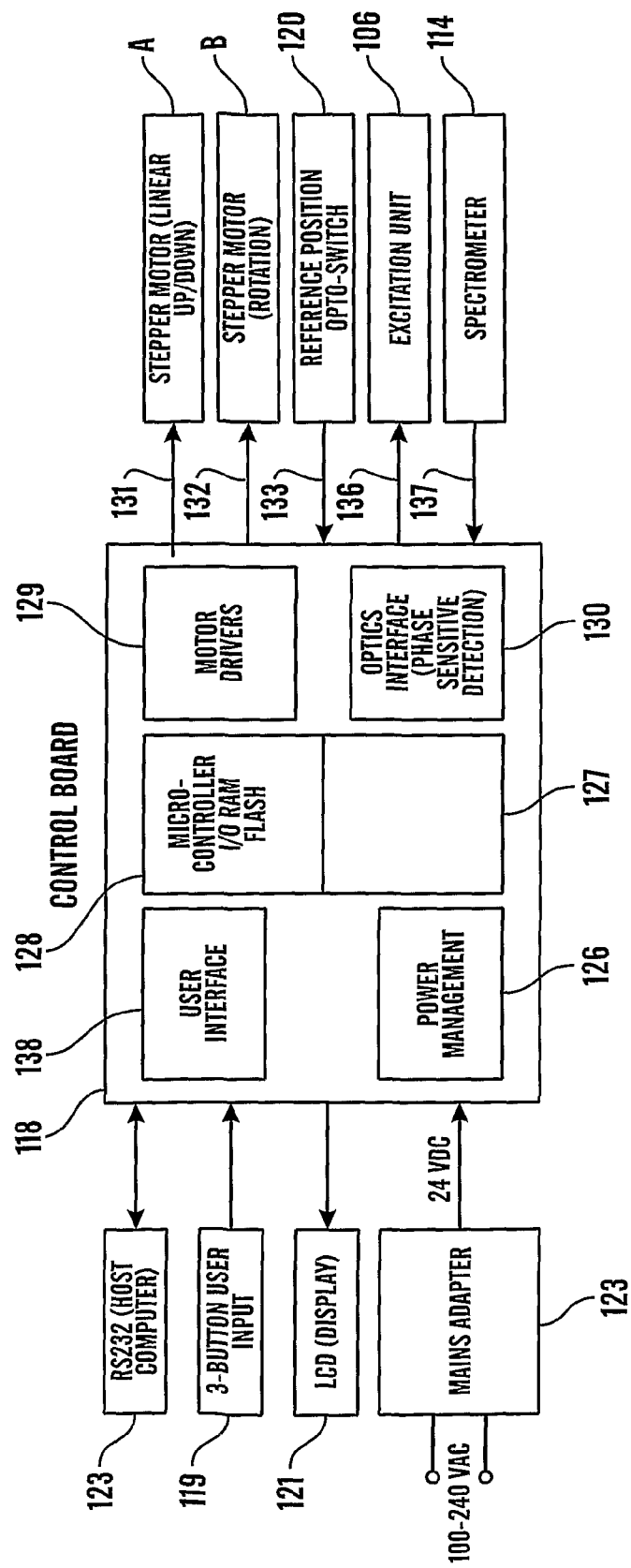
FIG. 4 is general arrangement of the electronic components of the apparatus for the detection and measurement of multiple targets.

We now refer to FIG. 4 that shows a general arrangement of the components which are mounted on the PCB 118.

Power is provided to the apparatus via a mains adaptor 123 and is provided to a power management module 126 on the board 118. The program and operating system to run the apparatus is contained within a microcontroller 128 attached to a field programmable gate array (FPGA) 127.

The optical components, and, in particular, the excitation unit 106 (excitation unit 5 in FIGS. 1 and 2) and the spectrometer 114 (spectrometer 33 in FIGS. 1 and 2,) are controlled by an optics interface module 130 via lines 136 and 137 respectively. In addition, there are provided a motor driver module 129 which includes 3 input/outputs, a first output 131 to a stepper motor A which provides a linear or axially up and down movement of the mounting means 102 (FIG. 3), a second output 132 to a stepper motor B which provides the rotation of the mounting means 102, and an input 133 which receives a signal from a Hall effect position switch 120 (see FIG. 3) which provides an indication of the exact position (axially and rotationally) of the mounting means 102.

A user interface module 138 is provided to send and receive signals via a link to a host computer 123, and to the buttons 119, and to the display 121.

The actuator 116 (FIG. 3) comprising the two stepper motors A and B may conveniently be provided by a HSI Hybrid Dual Motion Motor provided by the Haydon Switch Instrument, Inc.

The arrangement may be such that 200 steps of stepper motor B provide a single revolution of the shaft 117 (so each step equals 1.8°) and the linear movement may be 20 micron per step of the stepper motor A. This enables the target to be scanned in a very fine manner.

The source 106 may be provided by, for example, a continuously or intermittently driven xenon lamp or a continuously or intermittently driven light emitting diode.

In analysing the spectra using software in the computer, the following may be noted:
The spectral response is passed to the computer.
The software utilises multivariate data decomposition using a technique such as Principal Component Analysis to decompose.
The generated spectra data are stored as a matrix of data with rows of wavelength and columns of spectral acquisition positions.
Multivariate data decomposition (using techniques such as Principal Component Analysis, Target Factor Analysis (TFA), Principal Component Regression (PCR), Partial Least Squares Regression (PLS) and or Artificial Neural Network (ANN)) is used to decompose the data matrix assembled by the scanning action of the apparatus described.
The decomposed matrix is then compared with reference spectra of known compounds stored within the instrument's library.
The identified matching reference spectrum in the data matrix is then used to deduce the relative concentration in each scanned position.

Typically, a TFA least squares regression algorithm is used to estimate the absolute concentrations from the relative concentration using the known concentration (calibration) of the targeted reference spectra.

The degree of correlation between the reference and predicted spectrum within a spectral range is used to provide qualitative information within the spectral data matrix.

Typically, the generated spectra data set is assembled into a data table or matrix with rows being the wavelength index and columns being the spectral acquisition positions from the cartridge, slide or rod. The resulting data matrix may be analysed by a chemometric (multivariate) methods such as Principal Component Analysis (PCA), Target Factor Analysis (TFA), Principal Component Regression (PCR), Partial Least Squares Regression (PLS) and or Artificial Neural Network (ANN). Typically, reference spectra of toxins obtained from the measurement instrument are used as targets to deduce the presence and quantity of a toxin using Principal Component Analysis and a TFA least squares regression algorithm, respectively.

The invention is not restricted to the details of the foregoing examples.

For example, the radiation from the emission aperture 6 may be passed to the spectrometer by alternative optical means comprising a wave-guide, lenses, mirrors etc in place of the optical fibre 105.

The invention claimed is:

1. A method for the detection or determination of a target comprising a plurality of target compounds or derivatized target compounds, said method comprising immobilizing said target in a layer or band on a carrier, directing radiation at said target, said radiation being selected to cause the target compounds or derivatized target compounds of said target to emit relevant radiation, detecting said relevant radiation emitted by said target compounds or derivatized target compounds, said detected radiation comprising a mixture of spectra, storing spectral data of said detected radiation as a matrix of data of wavelength and spectral acquisition positions across the target, and analyzing said stored spectral data of said detected radiation to identify and quantify the plurality of target compounds or derivatized target compounds in said target using multivariate data decomposition.

2. The method as claimed in claim 1, wherein said spectral data is analyzed using principal component analysis to decompose the data.

3. The method as claimed in claim 1, wherein said detecting step comprises detecting said relevant radiation emitted by a defined part of said target, the method further comprising relatively moving the carrier and the defined part of the target, whereby the relevant radiation from different points of the target may be sensed.

4. The method as claimed in claim 3, wherein the relative movement includes linear and rotational movement.

5. A method for the detection or determination of a target comprising a plurality of target compounds or derivatized target compounds, said method comprising immobilizing said target in a layer or band on a carrier, directing radiation at said target, said radiation being selected to cause the target compounds or derivatized target compounds of said target to emit relevant radiation, said detected radiation comprising a mixture of spectra, detecting said relevant radiation emitted by said target compounds or derivatized target compounds in said layer or band, said detected radiation comprising a mixture of spectra, storing spectral data of said detected radiation as a matrix of data of wavelength and spectral acquisition positions across the target, and analyzing said stored spectral data of said detected radiation to identify and quantify the plurality of target compounds or derivatized target compounds in said target by comparing the stored spectral data with spectral data of reference spectra of known compounds to provide matching spectra.

6. The method as claimed in claim 5, wherein the matching reference spectra in the data matrix are used to identify the target compounds.

7. The method as claimed in claim 5, wherein the matching reference spectra in the data matrix are used to deduce the relative concentration of target compounds.

8. The method as claimed in claim 7, wherein a least squares method is used to estimate the absolute concentrations from the relative concentration using the reference spectrum of a known concentration of a known reference target compound.

9. The method as claimed in claim 8, wherein the degree of correlation between the reference and predicted spectrum within a spectral range provides qualitative information about the target.

10. An apparatus for the detection or determination of a target having a plurality of target compounds, or derivatized target compounds, said apparatus comprising means for mounting a carrier, the target being immobilized on a layer or band on said carrier, an excitation unit for emitting radiation and directing said radiation at said target, said radiation being selected to cause said target compounds or derivatized target compounds to emit relevant radiation, said detected radiation comprising a mixture of spectra, a detection unit that is sensitive to said relevant radiation emitted by said target compounds or derivatized target compounds in said layer or band comprising a spectrometer for producing a spectrum of said detected radiation, said detected radiation comprising a mixture of spectra, data storage means adapted to store spectral data of said spectrum of the detected radiation as a matrix of data with rows of wavelength and columns of spectral acquisition positions across the target, and means for analyzing said detected radiation to identify and quantify the plurality of target compounds in said target, wherein said means for analyzing said detected radiation is adapted to analyze said spectral data using multivariate data decomposition.

11. The apparatus as claimed in claim 10, wherein said means for analyzing said detected radiation is adapted to analyze said spectral data using principal component analysis to decompose the data.

12. An apparatus for the detection or determination of a target having a plurality of target compounds, or derivatized target compounds, said apparatus comprising means for mounting a carrier, the target being immobilized on a layer or band on said carrier, an excitation unit for emitting radiation and directing said radiation at said target, said radiation being selected to cause said target compounds or derivatized target compounds to emit relevant radiation, said detected radiation comprising mixture of spectra, a detection unit that is sensitive to said relevant radiation emitted by said target compounds or derivatized target compounds in said layer or band comprising a spectrometer for producing a spectrum of said detected radiation, data storage means adapted to store spectral data of said spectrum of the detected radiation as a matrix of data with rows of wavelength and columns of spectral acquisition positions across the target, and means for analyzing said detected radiation to identify and quantify the plurality of target compounds in said target wherein said means for analyzing said detected radiation is adapted to compare stored spectral data with spectral data of the matrix of decomposed data with reference spectra of known compounds to provide matching spectra.

13. The apparatus as claimed in claim 12, wherein said means for analyzing said detected radiation is adapted to identify the target compounds using the matching reference spectra.

14. The apparatus as claimed in claim 12, wherein said means for analyzing said detected radiation is adapted to deduce the relative concentration of target compounds using the matching reference spectra.

15. The apparatus as claimed in claim 14, wherein said means for analyzing said detected radiation is adapted to use a least squares method to estimate the absolute concentrations from the relative concentration using the reference spectrum of a known concentration of a known reference target compound.

16. The apparatus as claimed in claim 15, wherein said means for analyzing said detected radiation is adapted to use the degree of correlation between the reference and predicted spectrum within a spectral range to provide qualitative information within the spectral data matrix.

17. The apparatus as claimed in claim 12, wherein said excitation unit for emitting radiation and directing said radiation at said target comprises means for emitting radiation such as to cause fluorescence in said target.

18. The apparatus as claimed in claim 12, wherein said excitation unit for emitting radiation and directing said radiation at said target comprises means for emitting radiation such as to cause Raman scattering in said target.

19. The apparatus as claimed in claim 12, further comprising means for relatively moving the mounting means and the detection unit, whereby the relevant radiation from different points of the target may be sensed.

20. The apparatus as claimed in claim 19, wherein the means for relatively moving the mounting means and the detection unit comprises means for relatively moving the mounting means and the detection unit in a linear direction and means for relatively rotating the mounting means and the detection unit.

21. The apparatus as claimed in claim 12, wherein said detection unit includes an optical fiber for passing the radiation to the spectrometer.

22. The apparatus as claimed in claim 12, wherein said detection unit comprises an optical fiber for passing the radiation to the spectrometer.

23. The apparatus as claimed in claim 12, further comprising means for relatively moving the mounting means and the detection unit, whereby the relevant radiation from different points of the target may be sensed.

24. The apparatus as claim 12, wherein the means for mounting a carrier comprises means for immobilizing or isolating said target in at least one of a packing or coating or on a surface, a rod coated with the adsorbent for the target, a tube or cuvette coated internally with the adsorbent for the target, and a cartridge packed with a mineral or polymer adsorbent for the target.

25. The apparatus as claimed in claim 12, wherein the means for mounting a carrier comprises a slide selected from the group consisting of a slide of glass, a slide of metal, and a slide of plastic.

26. The apparatus as claimed in claim 12, wherein the means for relatively moving the mounting means and the detection unit comprises means for relatively moving the mounting means and the detection unit in such a manner as to scan the detection unit past all of the target.

27. The apparatus as claimed in claim 12, wherein the means for relatively moving the mounting means and the detection unit comprises means for relatively moving the mounting means and the detection unit in a linear direction and means for relatively rotating the mounting means and the detection unit.

28. The apparatus as claimed in claim 12, further comprising a processing unit that converts the output of the detection unit into a readable value related to the amount of target compound immobilized in the packing or coating or on a surface.

29. The apparatus as claimed in claim 12, wherein the means for relatively moving the mounting means and the detection unit comprises means for relatively moving the mounting means and the detection unit in such a manner as to scan the detection unit past all of the target.

30. An apparatus for the detection or determination of a target having a target compound or a derivatized target compound, said apparatus comprising means for mounting a carrier, the target being immobilized on a layer or band on said carrier, an excitation unit for emitting radiation and directing said radiation at said target, said radiation being selected to cause Raman scattering in said target compounds or derivatized target compounds, thereby emitting relevant radiation, a detection unit that is sensitive to said relevant radiation emitted by said target compounds or derivatized target compounds in said layer or band, said detection unit comprising a spectrometer to provide a spectrum of the radiation received, said detected radiation comprising mixture of spectra, data storage means adapted to store said spectrum of the detected radiation as a matrix of data with rows of wavelength and columns of spectral acquisition positions across the target, and means for analyzing said detected radiation to identify and quantify the target compound, said means for analyzing said detected radiation being adapted to analyze said spectral data using multivariate data decomposition.

31. The apparatus as claimed in claim 30, wherein said detection unit comprises an optical fiber for passing the radiation to the spectrometer.

32. The apparatus as claimed in claim 30, wherein said excitation unit comprises a laser to provide a laser beam of suitable wavelength to promote Raman excitation in the target.

33. The apparatus as claimed in claim 30, further comprising means for relatively moving the mounting means and the detection unit, whereby the relevant radiation from different points of the target may be sensed.

34. The apparatus as claim 30, wherein the means for mounting a carrier comprises means for immobilizing or isolating said target in at least one of a packing or coating or on a surface, a rod coated with the adsorbent for the target, a tube or cuvette coated internally with the adsorbent for the target, and a cartridge packed with a mineral or polymer adsorbent for the target.

35. The apparatus as claimed in claim 30, wherein the means for mounting a carrier comprises a slide selected from the group consisting of a slide of glass, a slide of metal, and a slide of plastic.

36. The apparatus as claimed in claim 30, wherein the means for relatively moving the mounting means and the detection unit comprises means for relatively moving the mounting means and the detection unit in a linear direction and means for relatively rotating the mounting means and the detection unit.

37. The apparatus as claimed in claim 30, further comprising a processing unit that converts the output of the detection unit into a readable value related to the amount of target compound immobilized in the packing or coating or on a surface.

* * * * *